(12) United States Patent
Hassan et al.

(10) Patent No.: US 8,278,494 B2
(45) Date of Patent: Oct. 2, 2012

(54) METHOD OF MAKING LINEAR ALKYLBENZENES

(75) Inventors: Abbas Hassan, Sugar Land, TX (US); Ebrahim Bagherzadeh, Sugar Land, TX (US); Rayford G. Anthony, College Station, TX (US); Gregory Borsinger, Chatham, NJ (US); Aziz Hassan, Sugar Land, TX (US)

(73) Assignee: H R D Corporation, Houston, TX (US)

( * ) Notice: Subject to any disclaimer, the term of this patent is extended or adjusted under 35 U.S.C. 154(b) by 53 days.

(21) Appl. No.: 12/144,459

(22) Filed: Jun. 23, 2008

(65) Prior Publication Data

US 2009/0005622 A1    Jan. 1, 2009

Related U.S. Application Data

(60) Provisional application No. 60/946,501, filed on Jun. 27, 2007.

(51) Int. Cl.
   *C07C 2/70*   (2006.01)
(52) U.S. Cl. ......... 585/447; 585/456; 585/455; 585/955
(58) Field of Classification Search .................. 585/447, 585/456, 455, 955
   See application file for complete search history.

(56) References Cited

U.S. PATENT DOCUMENTS

| | | | |
|---|---|---|---|
| 3,781,320 A | 12/1973 | Irwin | |
| 3,892,798 A | 7/1975 | Heeg et al. | |
| 3,996,012 A * | 12/1976 | Zucker | 422/211 |
| 4,724,269 A | 2/1988 | Suzki et al. | |
| 4,886,905 A | 12/1989 | Larkins, Jr. | |
| 4,914,029 A | 4/1990 | Caransa et al. | |
| 4,950,831 A | 8/1990 | Staton et al. | |
| 5,009,816 A | 4/1991 | Weise et al. | |
| 5,107,048 A * | 4/1992 | Huss et al. | 585/456 |
| 5,264,087 A | 11/1993 | Lowery et al. | |
| 5,382,358 A | 1/1995 | Yeh | |
| 5,451,348 A | 9/1995 | Kingsley | |
| 5,710,355 A | 1/1998 | Krishnamurti | |
| 5,756,714 A | 5/1998 | Antrim et al. | |
| 5,877,350 A | 3/1999 | Langer et al. | |
| 6,194,625 B1 | 2/2001 | Graves et al. | |
| 6,251,289 B1 | 6/2001 | Sherman | |
| 6,315,964 B1 * | 11/2001 | Knifton et al. | 422/190 |
| 6,368,366 B1 | 4/2002 | Langer et al. | |

(Continued)

FOREIGN PATENT DOCUMENTS

EP    1604969 A    12/2005

(Continued)

OTHER PUBLICATIONS

International Search Report, International Application No. PCT/US2008/068216, dated Jan. 21, 2009.

(Continued)

*Primary Examiner* — Thuan D Dang
(74) *Attorney, Agent, or Firm* — Timothy S. Westby; Porter Hedges LLP

(57) ABSTRACT

Methods and systems for the production of linear alkylbenzenes are described herein. The methods and systems incorporate the novel use of a high shear device to promote dispersion and mixing of one or more olefins (e.g. propylene) with an aromatic. The high shear device may allow for lower reaction temperatures and pressures and may also reduce reaction time with existing catalysts.

18 Claims, 2 Drawing Sheets

U.S. PATENT DOCUMENTS

| | | | |
|---|---|---|---|
| 6,368,367 | B1 | 4/2002 | Langer et al. |
| 6,383,237 | B1 | 5/2002 | Langer et al. |
| 6,693,213 | B1 | 2/2004 | Kolena et al. |
| 6,768,021 | B2 | 7/2004 | Horan et al. |
| 6,787,036 | B2 | 9/2004 | Long |
| 6,809,217 | B1 | 10/2004 | Colley et al. |
| 2003/0043690 | A1* | 3/2003 | Holl .............................. 366/279 |
| 2004/0052158 | A1 | 3/2004 | Holl |
| 2005/0033069 | A1 | 2/2005 | Holl et al. |
| 2006/0247482 | A1 | 11/2006 | Hope et al. |
| 2006/0272634 | A1 | 12/2006 | Nehmer et al. |

FOREIGN PATENT DOCUMENTS

| | | |
|---|---|---|
| EP | 1604969 A1 | 12/2005 |
| GB | 615624 | 10/1949 |
| JP | 61183235 A | 8/1986 |
| JP | 2000143706 A | 5/2000 |
| JP | 2002003505 A | 1/2002 |
| JP | 2002121353 A | 4/2002 |
| JP | 2007505201 A | 3/2007 |
| WO | 9843725 A | 10/1998 |
| WO | 2005108533 A2 | 11/2005 |
| WO | 2007023864 Y | 3/2007 |

OTHER PUBLICATIONS

Office Action Dated Apr. 20, 2010 for U.S. Appl. No. 12/411,660.
Office Action Dated Apr. 20, 2010 for U.S. Appl. No. 12/427,286.
Office Action Dated Apr. 23, 2010 for U.S. Appl. No. 12/568,155.
Office Action Dated Apr. 27, 2010 for U.S. Appl. No. 12/568,280.
Office Action Dated May 5, 2010 for U.S. Appl. No. 12/142,120.
Office Action Dated Jun. 25, 2009 for U.S. Appl. No. 12/142,447.
Office Action Dated Jan. 7, 2010 for U.S. Appl. No. 12/142,447.
Office Action Dated May 13, 2010 for U.S. Appl. No. 12/142,447.
Office Action Dated Feb. 4, 2010 for U.S. Appl. No. 12/492,721.
Office Action Dated Feb. 18, 2010 for U.S. Appl. No. 12/635,433.
Office Action Dated Feb. 18, 2010 for U.S. Appl. No. 12/635,454.
Office Action Dated May 14, 2010 for U.S. Appl. No. 12/137,441.
Office Action Dated Feb. 19, 2010 for U.S. Appl. No. 12/144,459.
Office Action Dated Sep. 2, 2009 for U.S. Appl. No. 12/142,433.
Office Action Dated Jan. 29, 2010 for U.S. Appl. No. 12/142,433.
Office Action Dated May 24, 2010 for U.S. Appl. No. 12/142,433.
Office Action Dated Apr. 30, 2010 for U.S. Appl. No. 12/141,191.
Office Action Dated Oct. 27, 2009 for U.S. Appl. No. 12/142,120.
Office Action Dated May 5, 2010 for U.S. Appl. No. 12/571,537.
Notice of Allowance for U.S. Appl. No. 12/796,358 dated Dec. 5, 2011; 14 pages.
European Search Report for Application No. 08780991.9 dated Apr. 14, 2011; 5 pages.
Final Office Action for U.S. Appl. No. 12/796,358 dated Feb. 24, 2011; 13 pages.
Canadian Office Action for Application No. 2689517 dated Jul. 14, 2011; 3 pages.
Chinese Office Action dated Jun. 7, 2012 for counterpart Chinese Application No. 200880021616.x; 9 pages.

* cited by examiner

METHOD OF MAKING LINEAR ALKYLBENZENES

CROSS-REFERENCE TO RELATED APPLICATIONS

This application claims the benefit under 35 U.S.C. §119 (e) of U.S. Provisional Patent Application No. 60/946,501, filed Jun. 27, 2007, the disclosure of which is hereby incorporated herein by reference.

BACKGROUND

1. Field of the Invention

This invention relates generally to the field of chemical reactions. More specifically, the invention relates to methods of making linear alkylbenzenes, that is, an alkyl aromatic compound wherein an atom of hydrogen in a benzene ring is substituted by a paraffin hydrocarbon chain, incorporating high shear mixing.

2. Background of the Invention

Alkylbenzenes have a wide range of technical uses. For instance alkylbenzenes with a number of carbon atoms in the side chain ranging between 8 and 16 are intermediates in the manufacture of sulfonated detergents. Alkylbenzene derivatives, such as alkyl benzene sulfonates, are among others, used in detergent and surfactant product applications. Environmental legislation requires that these products be biodegradable. Alkylbenzenes with a branched aliphatic chain are not decayed, departing from such with a linear chain, by aerobic bacteria and therefore tend to accumulate in water discharged from plants employing such detergents. It is well known that, to be biodegradable, it is important for the alkyl chain to be linear, i.e. with very little or no branching and low, if any, quaternary carbons. As such, linear alkylbenzenes have emerged as the dominant detergent intermediate since the early 1960s driven by the environmental need to produce biodegradable detergents.

The commercial development of linear alkylbenzenes has focused on the extraction of high purity linear paraffins derived from hydrotreated kerosene feedstock. Initially, these linear paraffins were dehydrogenated, at less than complete conversion, to linear internal mono-olefins. The dehydrogenation effluent, a mixture of olefins and paraffins, was used to alkylate benzene using hydrofluoric acid as the catalyst to produce linear alkylbenzenes. The conversion of the olefins to alkylbenzenes facilitated the separation of the unreacted linear paraffins by fractionation and their recycle to the dehydrogenation process. The resulting linear alkylbenzene product became the synthetic detergent intermediate for the production of linear alkylbenzene sulfonate, a major biodegradable synthetic surfactant. Linear alkylbenzene sulfonate remains the dominant workhorse surfactant but its position in North America and Western Europe is constantly challenged by detergent alcohol derivatives.

This detergent alkylate is formed by the reaction of an aromatic hydrocarbon with an olefinic hydrocarbon having from about 6 to 20 carbon atoms per molecule. A better quality detergent precursor normally results from the use of olefinic hydrocarbons having from 10-15 carbon atoms per molecule. In an embodiment, the alkylation reaction may be a Friedel-Crafts alkylation. Linear alkylbenzenes have been produced commercially via the following routes: 1) Dehydrogenation of n-paraffins to internal olefins followed by alkylation with benzene using a hydrofluoric acid (HF) catalyst; 2) Dehydrogenation of n-paraffins to internal olefins followed by alkylation with benzene using a fixed-bed of acidic, non-corrosive solid catalyst; 3) Chlorination of n-paraffins to form monochloroparaffins. The monochloroparaffins are subsequently alkylated with benzene in the presence of an aluminum chloride ($AlCl_3$) catalyst; and 4) Chlorination of n-paraffins to form chlorinated paraffins. The chlorinated paraffins are subsequently dehydrochlorinated to olefins (both alpha and internal). These olefins subsequently undergo benzene alkylation in the presence of an aluminum chloride catalyst. The preferred aromatic hydrocarbon is benzene but other hydrocarbons including toluene, xylene and ethylbenzene may also be alkylated in the same manner.

The preparation of linear alkylbenzenes by the catalytic alkylation of benzene with n-olefins may occur in the presence of Lewis acid catalysts, such as aluminum chloride boron trifluoride, hydrofluoric acid, sulfuric acid, phosphoric anhydride etc. In industrial practice, the two major catalysts for the alkylation of benzene with higher alpha or internal mono-olefins ($C_{10}$-$C_{16}$ detergent range olefins), are aluminum chloride and hydrofluoric acid. The HF-based process has become more prevalent than ones based on aluminum chloride. Alternatively, a mixture of n-olefins and chloroparaffins may be used as the alkylating agent of benzene, in the presence of aluminum chloride or aluminum in powder form as a catalyst.

The use of HF and $AlCl_3$ catalysts presents many challenges. For example, aluminum chloride is difficult to separate after reaction and produces a large amount of waste effluent. The desirability of avoiding the use of potentially hazardous chemicals like HF has motivated the development of improved mechanisms for the production of alkylbenzenes. The advances in making linear alkylbenzenes have focused on catalyst development or different reaction pathways. Reactions which involve olefinic hydrocarbons and are catalyzed by hydrogen fluoride usually proceed at a very fast rate. To reduce the amount of olefin polymerization and to promote production of a mono-alkylated aromatic product, the reactants are normally subjected to vigorous mixing and agitation at the initial contacting of the olefinic reactant with the hydrogen fluoride and aromatic reactant. The desired result is a uniform dispersion and intimate contacting of hydrocarbon and hydrogen fluoride phases and the avoidance of the formation of localized high temperatures or high hydrogen fluoride concentrations. Nothing has dealt with improving the mixing and dispersion of the reactants for lowering reaction time or lowering reaction pressure and temperature.

Consequently, there is a need for accelerated methods for making linear alkylbenzenes by improving the mixing of olefins into the liquid benzene phase.

BRIEF SUMMARY

Methods and systems for the preparation of linear alkylbenzenes are described herein. The methods and systems incorporate the novel use of a high shear device to promote dispersion and solubility of olefins in the aromatic liquid phase. The high shear device may allow for lower reaction temperatures and pressures and may also reduce alkylation time. Further advantages and aspects of the disclosed methods and system are described below.

In an embodiment, a method of making a linear alkylbenzene comprises introducing one or more olefins into an aromatic stream to form a reactant stream. The method also comprises subjecting said reactant stream to a shear rate of greater than about 20,000 $s^{-1}$ with a high shear device. Furthermore, the method comprises contacting the reactant stream with a catalyst to form a linear alkylbenzene.

In an embodiment, a system for the production of a linear alkylbenzene comprises at least one high shear device comprising a rotor and a stator. The rotor and the stator are separated by a shear gap in the range of from about 0.02 mm to about 5 mm. The shear gap is a minimum distance between the rotor and the stator. The high shear device is capable of producing a tip speed of the at least one rotor of greater than about 23 m/s (4,500 ft/min). In addition, the system comprises a pump configured for delivering a liquid stream to the high shear device. The system also comprises an alkylation reactor coupled to the high shear device. The reactor is configured for receiving said liquid stream from said high shear device In embodiments, the method comprises introducing an olefin into an aromatic stream. The method also comprises flowing the olefin and the aromatic stream through a high shear device so as to form dispersion with bubbles less than about 5 µm in diameter.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Figure 1:
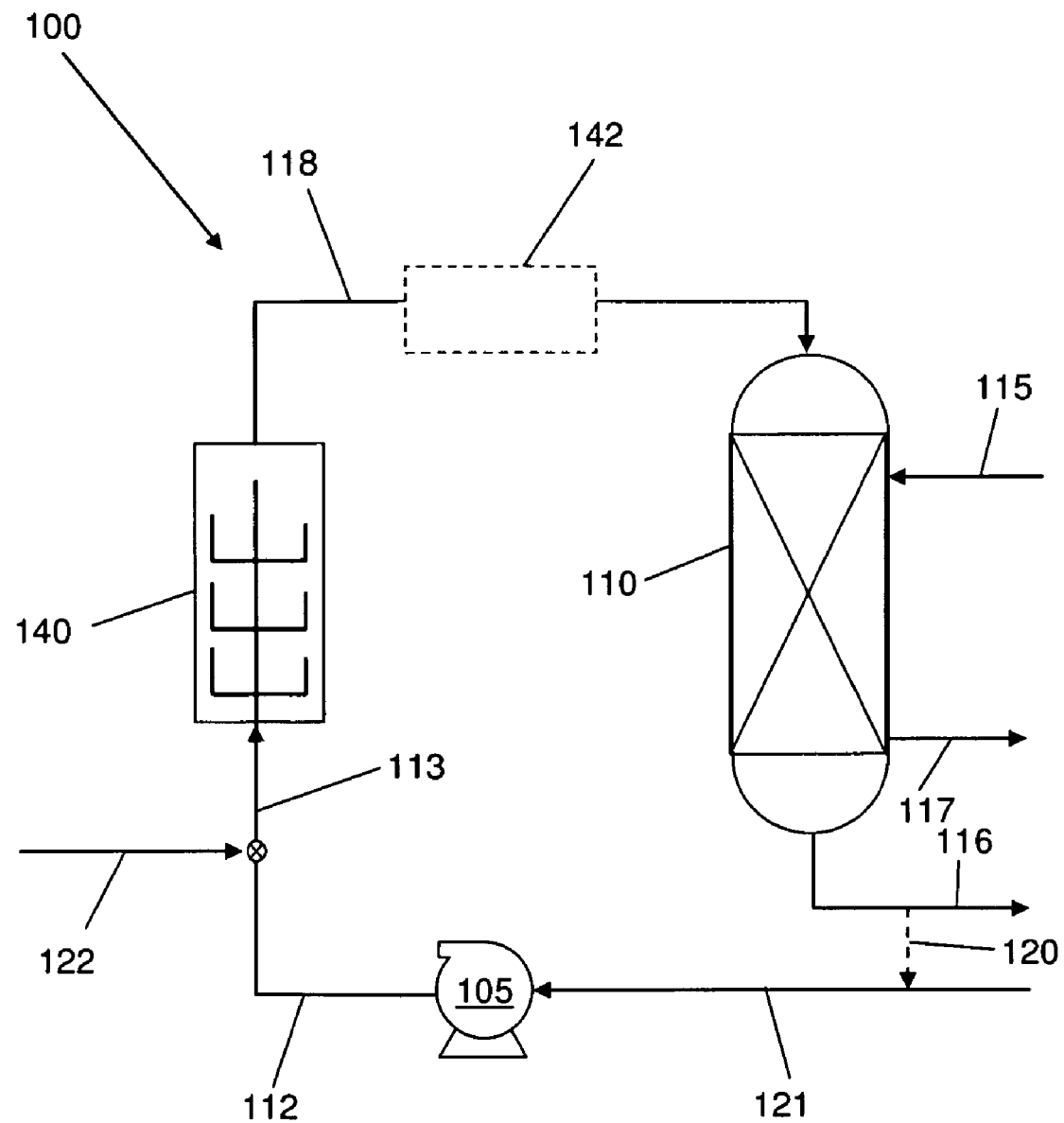
FIG. 1 illustrates a general flow diagram of an embodiment of a process using a high shear device.

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ".

DETAILED DESCRIPTION OF THE PREFERRED EMBODIMENTS

The process of the present disclosure for the linear alkylation of benzene comprises utilization of an external high shear mechanical device to provide rapid contact and mixing of chemical ingredients in a controlled environment in the reactor/mixer device. The high shear device is a mechanical reactor, mixer, or mill. The high shear device reduces the mass transfer limitations on the reaction and thus increases the overall reaction rate.

Chemical reactions involving liquids, gases and solids rely on the laws of kinetics that involve time, temperature, and pressure to define the rate of reactions. In cases where it is desirable to react two (or more) raw materials of different phases (e.g. solid and liquid; liquid and gas; solid, liquid and gas), one of the limiting factors in controlling the rate of reaction involves the contact time of the reactants. As used herein, "multi-phase" refers to a reaction involving reactions with two or more different phases. In the case of heterogeneously catalyzed reactions there is the additional rate limiting factor of having the reacted products removed from the surface of the catalyst to enable the catalyst to catalyze further reactants.

The alkylation of benzene with an olefin in the presence of a catalyst is a multiphase reaction. During the multiphase reaction, the phases separate spontaneously. It is desirable to provide the requisite intense mixing and contact time and to provide a means of allowing the hydrocarbon hydrogen fluoride mixture to separate into the respective liquid phases. The presently disclosed method and system whereby the two phases are intimately mixed to form an emulsion enhances contact surface between the reaction components, thus enhancing the reaction.

"Emulsion" refers to a liquefied mixture that contains two distinguishable substances (or "phases") that will not readily mix and dissolve together. Most emulsions have a "continuous" phase (or "matrix"), which holds therein discontinuous droplets, bubbles, and/or particles of the other phase or substance. Emulsions may be highly viscous, such as slurries or pastes, or may be foams, with tiny gas bubbles suspended in a liquid. As used herein, the term "emulsion" encompasses continuous phases comprising gas bubbles, continuous phases comprising particles (e.g., solid catalyst), continuous phases comprising droplets of a fluid that is substantially insoluble in the continuous phase, and combinations thereof.

In conventional reactors, contact time for the reactants and/or catalyst is often controlled by mixing which provides contact with two or more reactants involved in a chemical reaction. Embodiments of the disclosed method comprise an external high shear device to decrease mass transfer limitations and thereby more closely approach kinetic limitations. When reaction rates are accelerated, residence times may be decreased, thereby increasing obtainable throughput. Alternatively, where the current yield is acceptable, decreasing the required residence time allows for the use of lower temperatures and/or pressures than conventional processes. Furthermore, in homogeneous reactions, the disclosed process could be used to provide for uniform temperature distribution within the reactor thereby minimizing potential side reactions.

System for the Production of Linear Alkylbenzenes. A high shear alkylbenzene production system will now be described in relation to FIG. 1, which is a process flow diagram of an embodiment of a high shear system (HSS) 100 for the production of alkylbenzene via alkylation of benzene with olefins in the presence of a catalyst. The basic components of a representative system include external high shear device (HSD) 140, vessel 110, pump 105 and fluidized or fixed bed 142. As shown in FIG. 1, the high shear device is located external to vessel/reactor 110. Each of these components is further described in more detail below. Line 121 is connected to pump 105 for introducing reactant. Line 113 connects pump 105 to HSD 140, line 118 connects HSD 140 to fluidized or fixed bed 142 and line 119 connects bed 142 to vessel 110. Line 122 is connected to line 113. Line 117 is connected to vessel 110 for removal of unconverted reactants, and other by-products.

High shear devices (HSDs) such as a high shear device, or high shear mill, are generally divided into classes based upon their ability to mix fluids. Mixing is the process of reducing the size of inhomogeneous species or particles within the fluid. One metric for the degree or thoroughness of mixing is the energy density per unit volume that the mixing device generates to disrupt the fluid particles. The classes are distinguished based on delivered energy density. There are three classes of industrial mixers having sufficient energy density to consistently produce mixtures or emulsions with particle or bubble sizes in the range of 0 to 50 microns.

In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average particle sizes in the 0-1 micron range.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between low energy—high shear devices and homogenization valve systems, in terms of the mixing energy density delivered to the fluid, are colloid mills, which are classified as intermediate energy devices. The typical colloid mill configuration includes a conical or disk rotor that is separated from a complementary, liquid-cooled stator by a closely-controlled rotor-stator gap, which is commonly between 0.025 mm and 10.0 mm. Rotors are usually driven by an electric motor through a direct drive or belt mechanism. Many colloid mills, with proper adjustment, can achieve average particle sizes of 0.1 to 25 µm in the processed fluid. These capabilities render colloid mills appropriate for a variety of applications including colloid and oil/water-based emulsion processing such as that required for cosmetics, mayonnaise, silicone/silver amalgam formation, or roofing-tar mixing.

An approximation of energy input into the fluid (kW/L/min) can be estimated by measuring the motor energy (kW) and fluid output (L/min). Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance transcribed by the rotor tip, $2\pi R$, where R is the radius of the rotor (in meters, for example) times the frequency of revolution (in revolutions per minute). A colloid mill, for example, may have a tip speed in excess of 22.9 m/sec and may exceed 40 m/sec. For the purposes of this disclosure, the term "high shear" refers to mechanical rotor stator devices (e.g., colloid mills or rotor/stator mixers) that are capable of tip speeds in excess of 5.1 m/sec and require an external mechanically driven power device to drive energy into the stream of materials to be reacted. For example, in HSD 140, a tip speed in excess of 22.9 m/sec is achievable, and may exceed 40 m/sec. In some embodiments, HSD 140 is capable of delivering at least 300 L/h with a power consumption of about 1.5 kW at a nominal tip speed of at least 22.9 m/sec.

HSD 140 combines high tip speeds with a very small shear gap to produce significant friction on the material being processed. Accordingly, a local pressure in the range of about 1034.2 MPa and elevated temperatures at the tip of the shear mixer are produced during operation. In some embodiments, the energy expenditure of the high shear device is greater than 1000 W/m$^3$. In embodiments, the energy expenditure of HSD 140 is in the range of from about 3000 W/m$^3$ to about 7500 W/m$^3$. The shear rate is the tip speed divided by the shear gap width (minimal clearance between the rotor and stator). The shear rate generated in HSD 40 may be greater than 20,000 s$^{-1}$. In some embodiments the shear rate is at least 1,600,000 s$^{-1}$. In embodiments, the shear rate generated by HSD 140 is in the range of from 20,000 s$^{-1}$ to 100,000 s$^{-1}$. For example, in one application the rotor tip speed is about 40 m/sec and the shear gap width is 0.0254 mm, producing a shear rate of 1,600,000 s$^{-1}$. In another application the rotor tip speed is about 22.9 m/sec and the shear gap width is 0.0254 mm producing a shear rate of about 902,000 s$^{-1}$ HSD 140 is capable of highly mixing the reactants, some of which would normally be immiscible, at conditions such that at least a portion reacts to produce product. In some embodiments, HSD 140 comprises a colloid mill. Suitable colloidal mills are manufactured by IKA® Works, Inc. Wilmington, N.C. and APV North America, Inc. Wilmington, Mass., for example. In some instances, HSD 140 comprises the DISPAX REACTOR® of IKA® Works, Inc. Several models are available having various inlet/outlet connections, horsepower, nominal tip speeds, output rpm, and nominal flow rate. Selection of a particular device will depend on specific throughput requirements for the intended application, and on the desired particle size in the outlet dispersion from the high shear device. In some embodiments, selection of the appropriate mixing tools (generators) within HSD 140 may allow for catalyst size reduction/increase in catalyst surface area.

The high shear device comprises at least one revolving element that creates the mechanical force applied to the reactants. The high shear device comprises at least one stator and at least one rotor separated by a clearance. For example, the rotors may be conical or disk shaped and are separated from a complementary-shaped stator comprising a plurality of circumferentially-spaced high shear openings. For example, the rotors may be conical or disk shaped and may be separated from a complementary-shaped stator; both the rotor and stator may comprise a plurality of circumferentially-spaced teeth. In some embodiments, the stator(s) are adjustable to obtain the desired gap between the rotor and the stator of each generator (rotor/stator set). Grooves in the rotor and/or stator may change directions in alternate stages for increased turbulence. Each generator may be driven by any suitable drive system configured for providing the necessary rotation.

In some embodiments, the minimum clearance between the stator and the rotor is in the range of from about 0.0254 millimeters to about 3.175 millimeters. In certain embodiments, the minimum clearance between the stator and rotor is about 1.524 mm. In certain configurations, the minimum clearance between the rotor and stator is at least 1.778 mm. The shear rate produced by the high shear device may vary with longitudinal position along the flow pathway. In some embodiments, the rotor is set to rotate at a speed commensurate with the diameter of the rotor and the desired tip speed. In some embodiments, the colloidal mill has a fixed clearance between the stator and rotor. Alternatively, the colloid mill has adjustable clearance.

In some embodiments, HSD 140 comprises a single stage dispersing chamber (i.e., a single rotor/stator combination, a single generator). In some embodiments, high shear device 140 is a multiple stage inline colloid mill and comprises a plurality of generators. In certain embodiments, HSD 140 comprises at least two generators. In other embodiments, high shear device 140 comprises at least 3 high shear generators. In some embodiments, high shear device 140 is a multistage mixer whereby the shear rate (which varies proportionately with tip speed and inversely with rotor/stator gap) varies with longitudinal position along the flow pathway, as further described herein below.

In some embodiments, each stage of the external high shear device has interchangeable mixing tools, offering flexibility. For example, the DR 2000/4 DISPAX REACTOR® of IKA® Works, Inc. Wilmington, N.C. and APV North America, Inc. Wilmington, Mass., comprises a three stage dispersing module. This module may comprise up to three rotor/stator combinations (generators), with choice of fine, medium, coarse, and super-fine for each stage. This allows for creation of dispersions having a narrow distribution of the desired particle size. In some embodiments, each of the stages is operated with super-fine generator. In some embodiments, at least one of the generator sets has a rotor/stator minimum clearance of greater than about 5.08 mm. In alternative embodiments, at least one of the generator sets has a minimum rotor/stator clearance of greater than about 1.778 mm.

External high shear device 140 may be cooled as known to those of skill in the art. Liquid reactant, for example, may be used to cool the seal and thereby preheated as desired.

In embodiments, external high shear device 140 serves to intimately mix a liquid solution with a reactant stream 122. In embodiments, the resultant dispersion comprises microbubbles. In embodiments, the resultant dispersion comprises bubbles in the submicron size. In embodiments, the resultant dispersion has an average bubble size less than about 1.5 µm. In embodiments, the bubble size is from about 0.4 to about 1.5 µm. In embodiments, the high shear mixing produces hydrobubbles capable of remaining dispersed at atmospheric pressure for about 15 minutes.

As used herein, a high shear device is capable of dispersing or transporting, one phase or ingredient (e.g. liquid, solid, gas) into a main continuous phase (e.g. liquid) with which it would normally be immiscible or insoluble. In embodiment, a high shear device is a colloid mill for dispersing gas into an aqueous liquid, hereby creating an emulsion, or foam.

Figure 2:
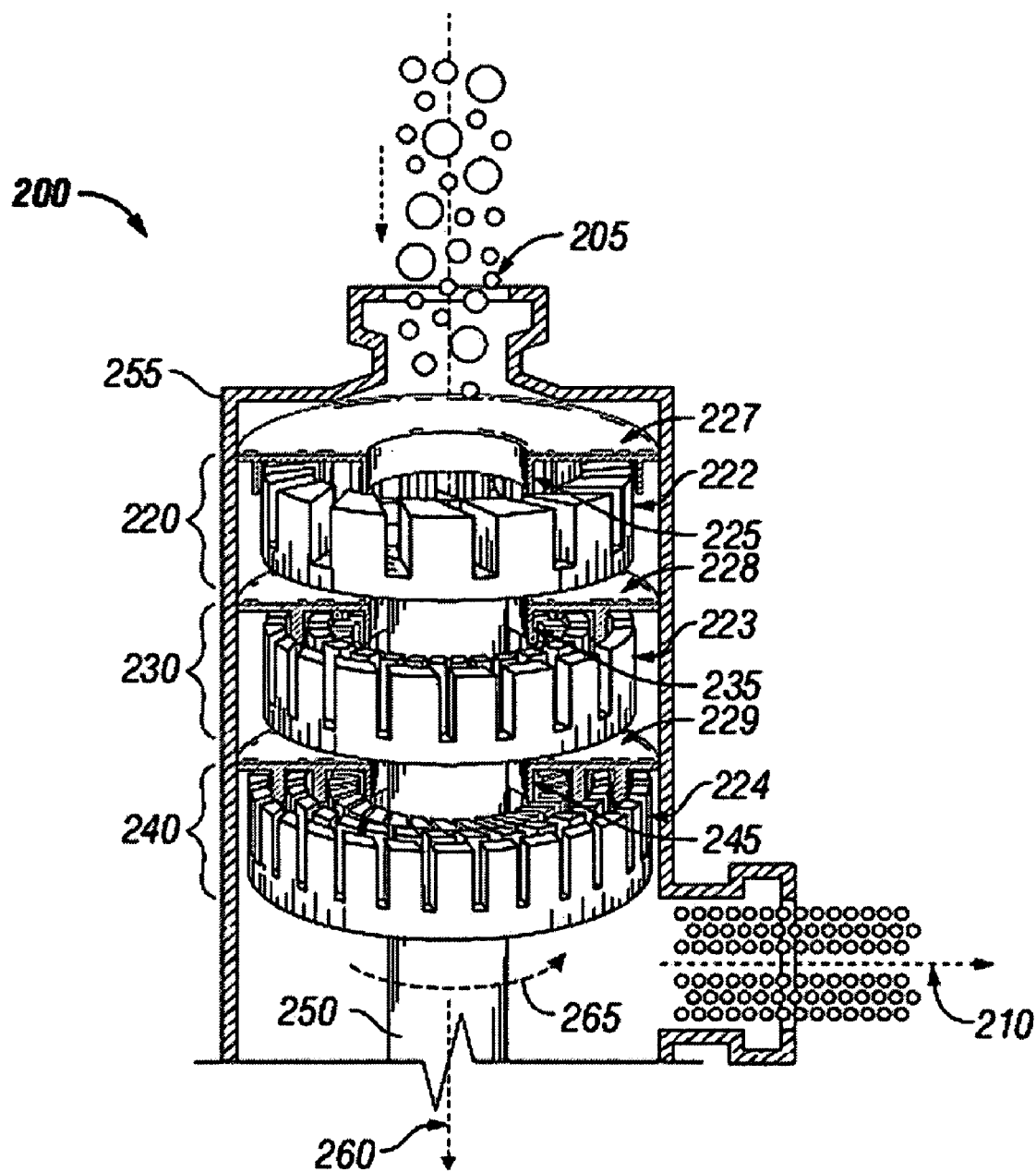
FIG. 2 illustrates a longitudinal cross-section view of a multi-stage high shear device, as employed in an embodiment of the system of FIG. 1.

Referring now to FIG. 2, there is presented a schematic diagram of a high shear device 200. High shear device 200 comprises at least one rotor-stator combination. The rotor-stator combinations may also be known as generators 220, 230, 240 or stages without limitation. The high shear device 200 comprises at least three generators.

The first generator 220 comprises rotor 222 and stator 227. The second generator 230 comprises rotor 223, and stator 228; the third generator comprises rotor 224 and stator 229. For each generator the rotor is rotatably driven by input 250. Stator 227 is fixably coupled to the high shear device wall 255.

The generators include gaps between the rotor and the stator. The first generator 220, comprises a first gap 225; the second generator 230 comprises a second gap 235; and the third generator 240 comprises a third gap 245. The gaps 225, 235, 245 are between about 0.025 mm and 10 mm wide. Alternatively, the process comprises utilization of a high shear device 200 wherein the gaps 225, 235, 245 are between about 0.5 mm and about 2.5 mm. In certain instances the gap is maintained at about 1.5 mm. Alternatively, the gaps 225, 235, 245 are different between generators 220, 230, 240. In certain instances, the gap 225 for the first generator 220 is greater than about the gap 235 for the second generator 230, which is in turn greater than about the gap 245 for the third generator. Each generator of the high shear device 200 has interchangeable mixing tools, offering flexibility.

Additionally, the width of the gaps 225, 235, 245 may comprise a coarse, medium, fine, and super-fine characterization. Rotors 222, 223, and 224 and stators 227, 228, and 229 may be toothed designs. Each generator may comprise two or more sets of rotor-stator teeth, as known in the art. Rotors 222, 223, and 224 may comprise a number of rotor teeth circumferentially spaced about the circumference of each rotor. Stators 227, 228, and 229 may comprise a number of stator teeth circumferentially spaced about the circumference of each stator. The rotor and the stator may be of any suitable size. In one embodiment, the inner diameter of the rotor is about 64 mm and the outer diameter of the stator is about 60 mm. In other embodiments, the inner diameter of the rotor is about 11.8 cm and the outer diameter of the stator is about 15.4 cm. The rotor and stator may have alternate diameters in order to alter the tip speed and shear pressures. In certain embodiments, each of three stages is operated with a super-fine generator, comprising a gap of between about 0.025 mm and about 3 mm. When a feed stream 205 including solid particles is to be sent through high shear device 200, the appropriate gap width is first selected for an appropriate reduction in particle size and increase in particle surface area. In embodiments, this is beneficial for increasing catalyst surface area by shearing and dispersing the particles.

High shear device 200 is fed a reaction mixture comprising the feed stream 205. Feed stream 205 comprises an emulsion of the dispersible phase and the continuous phase. Feed stream 205 may include a particulate solid catalyst component. Feed stream 205 is pumped through the generators 220, 230, 240, such that product dispersion 210 is formed. In each generator, the rotors 222, 223, 224 rotate at high speed relative to the fixed stators 227, 228, 229. The rotation of the rotors pumps fluid, such as the feed stream 205, between the outer surface of the rotor 222 and the inner surface of the stator 227 creating a localized high shear condition. The gaps 225, 235, 245 generate high shear forces that process the feed stream 205. The high shear forces between the rotor and stator functions to process the feed stream 205 to create the product dispersion 210.

The product dispersion 210 of gas particles, or bubbles, in a liquid comprises an emulsion. In embodiments, the product dispersion 210 may comprise a dispersion of a previously immiscible or insoluble gas, liquid or solid into the continuous phase. The product dispersion 210 has an average gas particle, or bubble, size less than about 1.5 µm; preferably the bubbles are sub-micron in diameter. In certain instances, the bubble size is from about 0.1 µm to about 1.0 µm. The high shear device 200 produces a gas emulsion capable of remaining dispersed at atmospheric pressure for about 15 minutes. For the purpose of this disclosure, an emulsion of gas particles, or bubbles, in the dispersed phase in product dispersion 210 that are less than 1.5 µm in diameter may comprise a micro-foam.

The high shear device 200 produces a gas emulsion capable of remaining dispersed at atmospheric pressure for at least about 15 minutes. For the purpose of this disclosure, an emulsion of gas particles, or bubbles, in the dispersed phase in product dispersion 210 that are less than 1.5 µm in diameter may comprise a micro-foam. Not to be limited by a specific theory, it is known in emulsion chemistry that sub-micron particles, or bubbles, dispersed in a liquid undergo movement primarily through Brownian motion effects. The bubbles in the emulsion of product dispersion 210 created by the high shear device 200 may have greater mobility through boundary layers of solid catalyst particles, thereby facilitating and accelerating the catalytic reaction through enhanced transport of reactants.

The rotor is set to rotate at a speed commensurate with the diameter of the rotor and the desired tip speed as described hereinabove. Transport resistance is reduced by incorporation of high shear device 200 such that the velocity of the reaction is increased by at least about 5%. Alternatively, the high shear device 200 comprises a high shear colloid mill that serves as an accelerated rate reactor (ARR). The accelerated rate reactor comprises a single stage dispersing chamber. The accelerated rate reactor comprises a multiple stage inline disperser comprising at least 2 stages.

Selection of the high shear device 200 is dependent on throughput requirements and desired particle or bubble size in the outlet dispersion 210. In certain instances, high shear device 200 comprises a DISPAX REACTOR® of IKA® Works, Inc. Wilmington, N.C. and APV North America, Inc. Wilmington, Mass. Model DR 2000/4, for example, comprises a belt drive, 4M generator, PTFE sealing ring, inlet flange 1" sanitary clamp, outlet flange ¾" sanitary clamp, 2HP power, output speed of 7900 rpm, flow capacity (water) approximately 300 l/h to approximately 700 l/h (depending on generator), a tip speed of from 9.4 m/s to about 41 m/s (about 1850 ft/min to about 8070 ft/min). Several alternative models are available having various inlet/outlet connections, horsepower, nominal tip speeds, output rpm, and nominal flow rate.

Without wishing to be limited to a particular theory, it is believed that the level or degree of high shear mixing is sufficient to increase rates of mass transfer and may also produce localized non-ideal conditions that enable reactions to occur that would not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, such as in homogeneous liquid phase reactions, the high shear device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming).

Vessel. Vessel or reactor 110 is any type of vessel in which a multiphase reaction can be propagated to carry out the above-described conversion reaction(s). For instance, a continuous or semi-continuous stirred tank reactor, or one or more batch reactors may be employed in series or in parallel. In some applications vessel 110 may be a tower reactor, and in others a tubular reactor or multi-tubular reactor. A catalyst inlet line 115 may be connected to vessel 110 for receiving a catalyst solution or slurry during operation of the system.

Vessel 110 may include one or more of the following components: stirring system, heating and/or cooling capabilities, pressure measurement instrumentation, temperature measurement instrumentation, one or more injection points, and level regulator (not shown), as are known in the art of reaction vessel design. For example, a stirring system may include a motor driven mixer. A heating and/or cooling apparatus may comprise, for example, a heat exchanger. Alternatively, as much of the conversion reaction may occur within HSD 140 in some embodiments, vessel 110 may serve primarily as a storage vessel in some cases.

Heat Transfer Devices. In addition to the above-mentioned heating/cooling capabilities of vessel 110, other external or internal heat transfer devices for heating or cooling a process stream are also contemplated in variations of the embodiments illustrated in FIG. 1. Some suitable locations for one or more such heat transfer devices are between pump 105 and HSD 140, between HSD 140 and vessel 110, and between vessel 110 and pump 105 when system 100 is operated in multi-pass mode. Some non-limiting examples of such heat transfer devices are shell, tube, plate, and coil heat exchangers, as are known in the art.

Pumps. Pump 105 is configured for either continuous or semi-continuous operation, and may be any suitable pumping device that is capable of providing greater than 2 atm pressure, preferably greater than 3 atm pressure, to allow controlled flow through HSD 140 and system 100. For example, a Roper Type 1 gear pump, Roper Pump Company (Commerce Ga.) Dayton Pressure Booster Pump Model 2P372E, Dayton Electric Co (Niles, Ill.) is one suitable pump. Preferably, all contact parts of pump 105 are stainless steel, for example, 316 stainless steel. In embodiments, for example, wherein corrosive substances will be pumped (e.g. sulfuric acid) it may be desirable to have gold plated contact surfaces. In some embodiments of the system, pump 105 is capable of pressures greater than about 20 atm. In addition to pump 105, one or more additional, high pressure pump (not shown) may be included in the system illustrated in FIG. 1. For example, a booster pump, which may be similar to pump 105, may be included between HSD 140 and vessel 110 for boosting the pressure into vessel 110.

Fluidized or Fixed Bed 142. A fluidized or fixed bed may be used to carry out the chemical reaction. The bed can be operated either in: (a) upflow, at a liquid velocity such that the particles are fluidized, or (b) downflow, in which case the bed is fixed. This method is used to continuously move the catalyst between the reactor and regeneration sections. A fluid bed is formed when a quantity of a solid particulate substance (usually present in a holding vessel) is forced to behave as a fluid; usually by the forced introduction of pressurized fluid, often a gas through the particulate medium. A fixed bed keeps the catalyst in one place converting the reactants to the desired product.

In embodiments, heating for a time is used to melt protective droplets on a catalyst. Additional reactants may be added over a time to bring the reactants to a desired temperature, for example, 35° C. In embodiments, the reactants are then introduced into high shear device 140 where the reactants may continuously circulated and the reaction continues over a time period sufficient to produce a desired product, for example, a product having a specified purity or property value, after which the reaction is terminated. In embodiments, pump 105 may be used to provide a controlled flow throughout high shear device 140 and system 100.

Production of Linear Alkylbenzenes. Embodiments of the process and system 100 will now be described in relation to accelerating the production of linear alkylbenzenes. Embodiments of the method comprise a process for alkylation of benzenes and its derivatives with olefins and paraffins in the presence of a catalyst dispersed in the liquid phase in a reactor 110. Embodiments of the process are characterized by the use of a high shear device 140 and introduction of olefins to a catalyst-benzene mixture before entering the high shear device 140. Other derivatives of benzene that may be used in conjunction with the process include without limitation, toluene, phenol, aniline, xylene, and the like. Generally, embodiments of the process are carried out by reacting a olefin containing about 1 to about 10 carbon atoms with benzene and/or its derivatives to obtain the desired alkylbenzene reaction product. In preferred embodiments, the olefin may be propylene or ethylene.

In a preferred embodiment, olefin may continuously be fed into aromatic stream 112 to form reactant stream 113. In high shear device 140, olefin and benzene are highly dispersed such that nanobubbles and microbubbles are formed for superior dissolution of olefin into solution. Once dispersed, the dispersion may exit high shear device 140 at high shear device outlet line 118. Stream 118 may optionally enter fluidized or fixed bed 142 in lieu of a slurry catalyst process. However, in a slurry catalyst embodiment, high shear outlet stream 118 may directly enter reactor 110 for alkylation. The reactant stream 113 may be maintained at the specified reaction temperature, using cooling coils in the reactor 110 to maintain reaction temperature. Alkylation products (e.g. linear alkylbenzenes) may be withdrawn at product stream 116. Product stream 116 may be directed to one or more strippers (not shown) for removing catalyst and purifying the alkylbenzene.

In an exemplary embodiment, the high shear device comprises a commercial disperser such as IKA® model DR 2000/4, a high shear, three stage dispersing device configured with three rotors in combination with stators, aligned in series. The disperser is used to create the dispersion of olefins in the liquid medium comprising water (i.e., "the reactants"). The rotor/stator sets may be configured as illustrated in FIG. 2, for example. The combined reactants enter the high shear device via line 113 and enter a first stage rotor/stator combination having circumferentially spaced first stage shear openings. The coarse dispersion exiting the first stage enters the second rotor/stator stage, which has second stage shear openings. The reduced bubble-size dispersion emerging from the second stage enters the third stage rotor/stator combination having third stage shear openings. The dispersion exits the high shear device via line 118. In some embodiments, the shear rate increases stepwise longitudinally along the direction of the flow. For example, in some embodiments, the shear rate in the first rotor/stator stage is greater than the shear rate in subsequent stage(s). In other embodiments, the shear rate is substantially constant along the direction of the flow, with the stage or stages being the same. If the high shear device includes a PTFE seal, for example, the seal may be cooled using any suitable technique that is known in the art. For example, the reactant stream flowing in line 113 may be used to cool the seal and in so doing be preheated as desired prior to entering the high shear device.

The rotor of HSD 140 is set to rotate at a speed commensurate with the diameter of the rotor and the desired tip speed. As described above, the high shear device (e.g., colloid mill) has either a fixed clearance between the stator and rotor or has adjustable clearance. HSD 140 serves to intimately mix the olefin vapor and the reactant liquid. In some embodiments of the process, the transport resistance of the reactants is reduced by operation of the high shear device such that the velocity of the reaction (i.e. reaction rate) is increased by greater than a factor of about 5. In some embodiments, the velocity of the reaction is increased by at least a factor of 10. In some embodiments, the velocity is increased by a factor in the range of about 10 to about 100 fold. In some embodiments, HSD 140 delivers at least 300 L/h with a power consumption of 1.5 kW at a nominal tip speed of at least 4500 ft/min, and which may exceed 7900 ft/min (140 m/sec). Although measurement of instantaneous temperature and pressure at the tip of a rotating shear unit or revolving element in HSD 140 is difficult, it is estimated that the localized temperature seen by the intimately mixed reactants may be in excess of 500° C. and at pressures in excess of 500 kg/cm$^2$ under high shear conditions. The high shear may result in formation micron or submicron-sized bubbles. In some embodiments, the resultant dispersion has an average bubble size less than about 1.5 μm.

Accordingly, the dispersion exiting HSD 140 via line 118 comprises micron and/or submicron-sized gas bubbles. In some embodiments, the mean bubble size is in the range of about 0.4 μm to about 1.5 μm. In some embodiments, the mean bubble size is less than about 400 nm, and may be about 100 nm in some cases. In many embodiments, the microbubble dispersion is able to remain dispersed at atmospheric pressure for at least 15 minutes.

Once dispersed, the resulting olefin/water dispersion exits HSD 140 via line 118 and feeds into vessel 110, as illustrated in FIG. 1. As a result of the intimate mixing of the reactants prior to entering vessel 110, a significant portion of the chemical reaction may take place in HSD 140, with or without the presence of a catalyst. Chemical reactions which involve olefinic hydrocarbons and which are catalyzed usually proceed at a very fast rate. To reduce the amount of olefin polymerization and to promote the production of a monoalkylated aromatic product, the reactants are normally subjected to vigorous mixing and agitation at the point of initial contact of the olefinic hydrocarbons and the liquid-phase catalyst (i.e. hydrogen fluoride). The desired result is a uniform dispersion and intimate contacting of the hydrocarbon and catalyst phases and the avoidance of localized high temperatures or localized high concentrations of either the olefinic hydrocarbon or the hydrogen fluoride. Accordingly, in some embodiments, reactor/vessel 110 may be used primarily for heating and separation of volatile reaction products from the alkylbenzene product. Alternatively, or additionally, vessel 110 may serve as a primary reaction vessel where most of the alkylbenzene product is produced. Vessel/reactor 110 may be operated in either continuous or semi-continuous flow mode, or it may be operated in batch mode. The contents of vessel 110 may be maintained at a specified reaction temperature using heating and/or cooling capabilities (e.g., cooling coils) and temperature measurement instrumentation. Pressure in the vessel may be monitored using suitable pressure measurement instrumentation, and the level of reactants in the vessel may be controlled using a level regulator (not shown), employing techniques that are known to those of skill in the art. The contents are stirred continuously or semi-continuously.

The reaction may proceed under temperature and pressure conditions commonly employed in such catalytic alkylation reactions. In embodiments, the reaction temperature may range from about 0° C. to about 80° C., preferably from about 30° C. to about 60° C. In addition, the reaction pressure may range from about 1 atm to about 10 atm, preferably from about 1 atm to about 5 atm.

In embodiments, the linear alkylbenzenes produced may have the following formula:

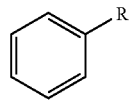

where R is an alkyl group having from 1 to 20 carbon atoms and R may be branched or unbranched.

In an alternative embodiment, high shear device 140 may serve as the alkylation reactor. That is, high shear device 140 may be heated to a specified temperature to initiate the alkylation reaction. High shear device 140 increases the dispersion and solubility of olefin into the liquid aromatic phase for improved mass transfer and reaction kinetics.

Catalyst. A catalyst may be introduced into the vessel via line 115, as an aqueous or nonaqueous slurry or stream. Alternatively, or additionally, catalyst may be added elsewhere in the system 100. For example, catalyst solution or slurry may be injected into line 121. In general, the catalyst is an aluminum halide or aluminum powder catalyst. In further embodiments, the catalyst may comprise halides of titanium, zirconium, vanadium, chromium, iron, or combinations thereof. A suitable catalyst may also be based on a Lewis acid, for example, HF and $AlCl_{3-}$. Catalyst may be fed into reactor 110 through catalyst feed stream 115. The catalyst concentration in the reactor appreciably affects the rate of alkylation. For example, the most advantageous concentration corresponds to 1 to 5 gr. aluminum halide to liter of benzene. The amount of benzene present during the alkylation will depend on the conversion selectivity to alkylbenzene. In general, the greater the stoichiometric excess of benzene, the greater the selectivity to alkylbenzene.

Multiple Pass Operation. In the embodiment shown in FIG. 1, the system is configured for single pass operation, wherein the output from vessel 110 goes directly to further processing for recovery of alkylbenzene product. In some embodiments it may be desirable to pass the contents of vessel 110, or a liquid fraction containing unreacted olefin, through HSD 140 during a second pass. In this case, line 116 is connected to line 121 via dotted line 120, and the recycle stream from vessel 110 is pumped by pump 105 into line 113 and thence into HSD 140. Additional olefins may be injected via line 122 into line 113, or it may be added directly into the high shear device (not shown).

Multiple High Shear Devices. In some embodiments, two or more high shear devices like HSD 140, or configured differently, are aligned in series, and are used to further enhance the reaction. Their operation may be in either batch or continuous mode. In some instances in which a single pass or "once through" process is desired, the use of multiple high shear devices in series may also be advantageous. In some embodiments where multiple high shear devices are operated in series, vessel 110 may be omitted. In some embodiments, multiple high shear devices 140 are operated in parallel, and the outlet dispersions therefrom are introduced into one or more vessel 110.

While the preferred embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

We claim:

1. A method of producing a linear alkylbenzene, the method comprising:
    a) introducing one or more olefins into an aromatic stream to form a reactant stream; and
    b) subjecting said reactant stream to a shear rate of greater than about 20,000s$^{-1}$ and to a high shear mixing at a tip speed of at least about 23 m/s in a high shear device to form gas bubbles having a mean diameter of less than 100 nm to produce a high shear product stream, wherein the high shear device comprises at least one generator comprising a rotor and a complementarily-shaped stator; and
    c) separating linear alkylbenzene from the high shear product stream, wherein said linear alkylbenzene is formed at a temperature in the range of from about 0° C. to about 60° C.

2. The method of claim 1 further comprising contacting the aromatic stream with a catalyst before (a), contacting the high shear product with a catalyst after (b), or both.

3. The method of claim 1 further comprising combining a catalyst with at least one selected from the group consisting of the one or more olefins, the aromatic stream, the reactant stream and the high shear product stream.

4. The method of claim 2 wherein the catalyst comprises a Lewis acid.

5. The method of claim 1 wherein the linear alkylbenzene comprises dodecylbenzene.

6. The method of claim 1 further comprising introducing the high shear product to a fluid or fixed bed containing an alkylation catalyst.

7. The method of claim 3, wherein the catalyst is selected from the group consisting of aluminum halides, titanium halides, zirconium halides, iron halides, vanadium halides, chromium halides, and combinations thereof.

8. The method of claim 1 wherein the linear alkylbenzene has the formula:

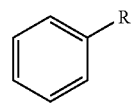

wherein R is an alkyl group having from 1 to 20 carbon atoms and R may be branched or unbranched.

9. The method of claim 1 wherein the olefin comprises from 2 to 10 carbon atoms.

10. The method of claim 1 wherein the aromatic stream comprises at least one selected from the group consisting of benzene, toluene, phenol, aniline, xylene and ethylbenzene.

11. The method of claim 1 wherein the high shear product stream comprises a dispersion of olefin-containing bubbles.

12. The method of claim 11 wherein the olefin-containing bubbles have an average bubble diameter of less than about 5 µm.

13. The method of claim 11 wherein the olefin-containing bubbles have a submicrometer average bubble diameter.

14. The method of claim 1 wherein (c) comprises stripping.

15. The method of claim 1 further comprising recycling at least a portion of the high shear product stream to the high shear device, introducing at least a portion of the high shear product stream into another high shear device, or both.

16. The method of claim 1 wherein the high shear device comprises at least two generators.

17. The method of claim 3 wherein the catalyst is selected from the group consisting of hydrofluoric acid and aluminum chloride.

18. The method of claim 1 wherein (b) comprises subjecting the reactant stream to high shear mixing at a tip speed of at least about 40 m/s.

* * * * *